United States Patent [19]
Conrad

[11] Patent Number: 5,151,250
[45] Date of Patent: Sep. 29, 1992

[54] AUTOMATIC PURGE METHOD FOR OZONE GENERATORS

[76] Inventor: Richard H. Conrad, P.O. Box 1300, Pt. Reyes Station, Calif. 94956

[21] Appl. No.: 497,126

[22] Filed: Mar. 21, 1990

[51] Int. Cl.$^5$ .............................. C02F 1/78; F15C 1/06; F15D 1/02
[52] U.S. Cl. .......................................... 422/2; 422/28; 210/760; 210/192; 210/136; 137/614.2; 137/893; 137/895
[58] Field of Search ...................... 422/2, 28; 210/760, 210/192, 136; 137/614.2, 893, 895

[56] References Cited

U.S. PATENT DOCUMENTS

| | | | |
|---|---|---|---|
| 2,606,150 | 8/1952 | Thorp | 210/760 |
| 3,445,001 | 5/1969 | Raus | 210/192 |
| 3,549,528 | 12/1970 | Armstrong | 210/192 X |
| 3,989,461 | 11/1976 | Skocypec et al. | 422/2 X |
| 4,261,950 | 4/1981 | Bainbridge et al. | 422/116 X |
| 4,913,192 | 4/1990 | Varva | 137/893 X |

Primary Examiner—Robert J. Warden
Assistant Examiner—Stephanie Blythe
Attorney, Agent, or Firm—Larry D. Johnson

[57] ABSTRACT

A negative pressure flow regulation and automatic purge method which provides an improved ozone delivery system for use with ozone generators using venturi devices or other negative-pressure ozone injection schemes, such as in ozone water purification systems. The system comprises four components in a particular arrangement: a first check valve and a needle valve or orifice in the ozone line immediately following the ozone generator, a second check valve at or near the venturi end of the ozone line, and a vacuum reservoir volume consisting of the combined volume of a vacuum bottle and the length of ozone line between the needle valve and the second check valve. The system maintains a near-ambient pressure in the ozone generator during operation, and after shutdown it provides an automatic purge of the ozone generator, prevents back-diffusion of ozone into the gas supply line and firmly seats the safety check valve in the ozone delivery line.

19 Claims, 1 Drawing Sheet

AUTOMATIC PURGE METHOD FOR OZONE GENERATORS

BACKGROUND OF THE INVENTION

1. Field of the Invention

This invention relates generally to ozone delivery systems, and more specifically to an automatic purging method for use in ozone systems which employ negative pressure to inject ozone into a fluid to be treated.

2. Description of the Prior Art

Ozone is a very powerful gaseous reactant, and its usefulness has been well established for many years in a wide range of industrial applications. Recently its value in all types of water purification applications has been coming to the fore because of its ability to act as a powerful oxidant, microflocculant and disinfectant without producing toxic side-products.

Many ozone systems utilize negative pressure such as from a venturi to draw ozone from an ozone generator into the water to be treated. It would be desirable to provide some means of automatically purging the ozone out of the generator after system shutdown in order to prolong the life of the seals inside the generator (which are usually ozone resistant but not ozone inert). In air, ozone has a half-life of approximately one day, and since in some systems the generator may be on for only an hour at a time, with six hour intervals during which it is off, a purge with air (or oxygen) after each shutdown would prevent the seals from being exposed to high concentrations of ozone during off periods and would greatly lengthen their life. Purging after generator shutdown would also prevent the harmful diffusion of ozone backwards into the inlet tubing, flowmeter, moisture and flow sensors, air filter and other air preparation equipment located in the gas supply line upstream of the generator. Although a check valve immediately before the generator could prevent this back-diffusion, the cracking pressure of the check valve would have to be high enough for it to be able to reseat itself since there is no backpressure to assist such seating. The cracking pressure required would lower the operating pressure inside the ozone generator, thereby decreasing its output of ozone.

In systems employing a venturi, the gas flow is motivated by a water pump, and the obvious way to purge an ozone generator operating with a venturi would be to include a switch which turns off the power to the generator some time interval before the water pump goes off. There are two disadvantages to this: 1) one cannot anticipate the shut-down of the water pump in all situations; and 2) in applications such as spas operating with ozone as the sole disinfectant, where the flow of water usually carries high concentrations of bacteria out of the filter (which bacteria are normally immediately killed by the addition of ozone and therefore never reach the spa), it is undesirable to run the circulation pump for even a few seconds without the ozone generator being on.

An additional problem in managing shutdown in prior art ozone generation systems which employ a venturi to inject ozone into water concerns the check valve needed in the ozone delivery line to prevent water from backing up towards the generator after shutdown (or, in situations where the point of ozone injection is above the water level of a vented vessel such as a tank, pool or spa, to prevent air from being sucked through the valve in the forward direction which would cause the plumbing to drain into the vessel and thereby lose its prime). In the majority of systems there is no backpressure after shutdown to firmly re-seat the check valve. Thus for reliable operation, the cracking pressure must be rather high, and this high cracking pressure greatly decreases the efficiency of the venturi which must draw ozone through the check valve.

SUMMARY OF THE INVENTION

The negative pressure automatic purge and flow regulation method of the present invention provides an improved ozone delivery system for use with ozone generators using venturi devices or other negative-pressure ozone injection schemes, such as in ozone water purification systems. This novel system comprises four components (preferably all inert to ozone) in a particular arrangement: a first one-way check valve and a needle valve or orifice in the ozone line immediately following the ozone generator, a second one-way check valve at or near the venturi end of the ozone line, and a vacuum reservoir volume consisting of the combined volume of a vacuum bottle and of the length of ozone line between the needle valve and the second check valve. The vacuum reservoir volume that is necessary to provide a purge consisting of a particular volume of dry air depends on the operational vacuum within the reservoir volume and the cracking pressure of the first check valve.

The negative pressure flow-regulating system with automatic vacuum purge provides the following benefits:

1. It enables an ozone generator to be operated at a positive or slightly negative pressure (any significant vacuum in the generator itself is undesirable because then the partial pressure of oxygen entering the corona is less and therefore the concentration of ozone generated is decreased), while at the same time allowing the venturi to be operated at a higher vacuum, which is the venturi's most stable and efficient mode of operation. This higher vacuum also allows the use of a stronger spring in the second check valve and enhances the back-suction upon shutdown benefit described below (both of these items contribute to more reliable functioning of the check valve while the system is off). Additionally, the higher vacuum provides more purging volume upon shutdown.

2. It allows precise needle-valve control of the air flow through the ozone generator while the water pump is on, without varying the pressure inside the generator.

3. It automatically purges the ozone generator of ozone upon shutdown, thus extending the life of the generator and its seals. This automatic purge takes effect regardless of whether the shutdown is anticipated or unexpected.

4. It solves the problem of back-diffusion of ozone upon shutdown by automatically pulling dry gas through the ozone generator and first check valve into the vacuum bottle immediately after each shut-down, thus protecting fittings, tubing, and air flowmeter and other sensors from exposure to residual ozone.

5. It provides the highly desirable additional benefit of creating a powerful back-suction upon shutdown (in the reverse direction from normal ozone flow) to firmly seat the seal of the second check valve which enables it to reliably prevent water from backing up into the ozone line (or to prevent air from leaking into the water pipes to cause loss of prime when the second check valve is below the waterline) when the system is off. In either case this static back-suction provides a very beneficial assist to the spring inside the second check valve, which of itself, even with the relatively high operational vacuum of the system of the present invention, cannot always be made strong enough to do these jobs as well as desired by itself because its cracking pressure would then be so high as to interfere with normal operation. In addition, the use of two check valves provides a desirable extra margin of safety.

Thus, the method of the present invention addresses and solves the above-mentioned problems of prior art ozone delivery systems at shutdown: the need for an automatic purge, the need to prevent back-diffusion of ozone, and the need to firmly seat the check valve in the ozone delivery line. In addition it provides a gas flow regulation means which maintains a near-ambient pressure in the ozone generator during operation while allowing the venturi to function at a considerable vacuum, where its operation is most stable and efficient.

DETAILED DESCRIPTION OF THE INVENTION

Figure 1:
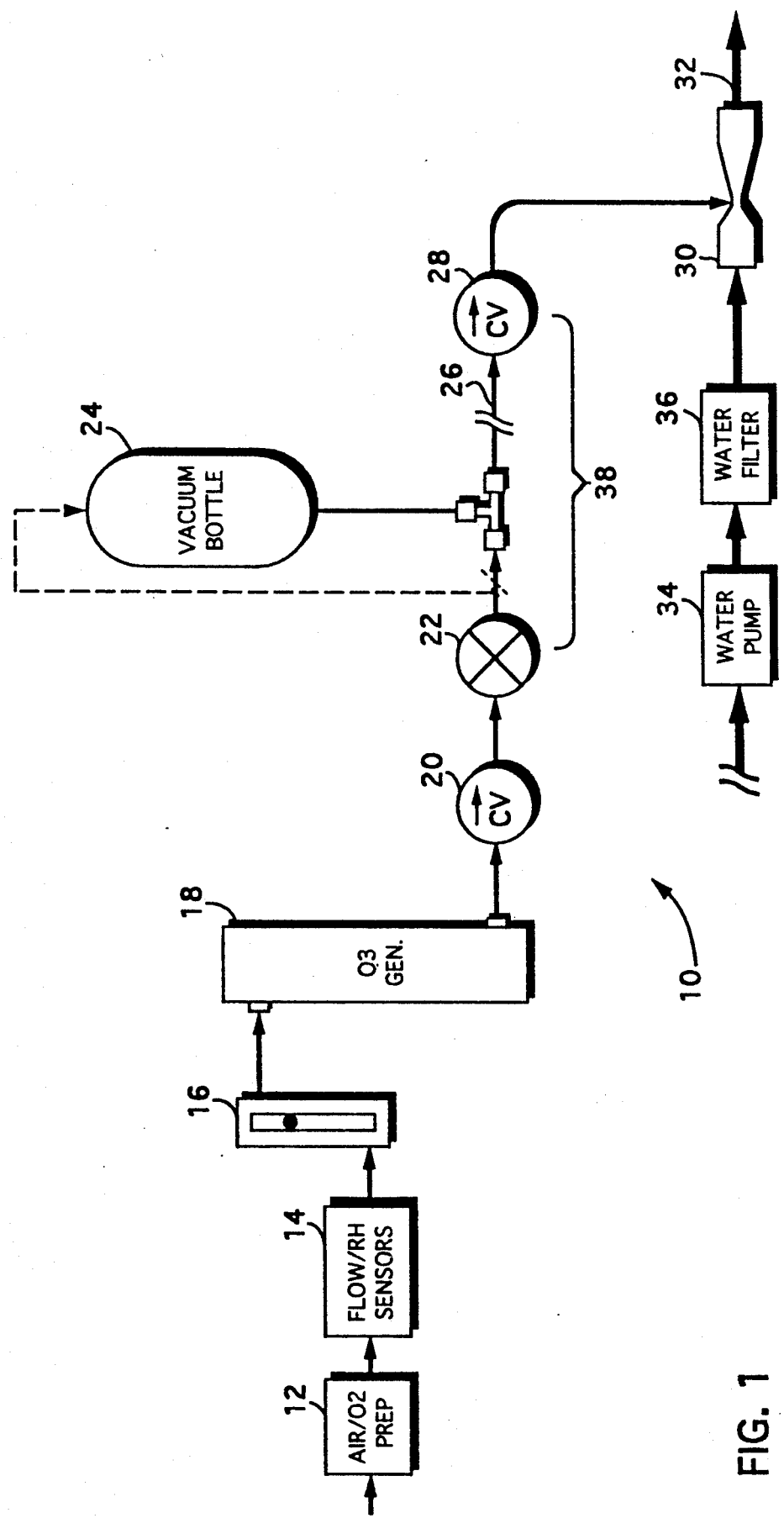
FIG. 1 is a schematic view of a negative pressure flow regulation and automatic vacuum purge system of the present invention in a water purification application.

FIG. 1 is a schematic view of a negative pressure flow regulation and automatic vacuum purge system 10 in a water purification application utilizing an ozone generator and a venturi. During normal operation air or oxygen from an air/oxygen preparation unit 12 (which may include an air drier or dessicant and filters) passes through flow and relative humidity sensors 14, a flowmeter 16, an ozone generator 18, a first check valve 20, a needle valve or orifice 22, past or through a vacuum bottle 24 (which can either have a single opening as shown or can have a separate entrance and exit, as indicated in phantom lines), an ozone delivery line 26, a second check valve 28, a venturi 30, and ultimately into a water line 32, which may include a water pump 34 and a water filter 36.

The needle valve 22, which is placed between the ozone generator 18 and the vacuum bottle 24, serves to adjust the rate of flow of dry air or oxygen through the ozone generator and to separate the system into two regions of different pressure: a positive or a slightly negative pressure in the generator 18 (if negative, necessarily slight so as not to diminish ozone output, as explained above), and a greater negative pressure in a reservoir 38 defined by the total contiguous volume of tubing, vacuum bottle, fittings, and any other components existing between the needle valve 22 and the second check valve 28. The greater the operational vacuum in the reservoir, the larger the volume of air purge for a given reservoir size and the better the functioning of the second check valve. The first check valve 20 could alternatively be positioned between the needle valve 22 and the vacuum bottle 24. In cases where a needle valve adjustment is not needed, the check valve itself can be designed to also act as the orifice, thus obviating the need for a separate orifice.

Both check valves 20, 28 are necessary because without the first one, after shutdown the ozone which had been purged out of the generator 18 by being sucked into the vacuum bottle 24 or reservoir 38 could diffuse back into the generator again, and without the second one the vacuum in the reservoir would pull water from the venturi 30 into the reservoir instead of pulling dry air through the ozone generator. Without the restriction of the needle valve or orifice 22 after the generator, there would be very little negative operational pressure in the reservoir and the gas flow rate through the generator would be overly high. If a needle valve or orifice were placed before the generator in order to limit the flow rate, as is done in some prior art systems, then the vacuum in the generator would be too high for efficient ozone generation.

With the water pump on, typical gas pressures could be, for example (with first and second check valve cracking pressures of 1.5 psi): $-10.5$ psi at the venturi, $-9$ psi in the vacuum reservoir and $-.1$ psi in the ozone generator. When the water pump shuts off (the power to the ozone generator going off simultaneously), the venturi stops aspirating, and the $-9$ psi in the vacuum reservoir sucks the seal of the second check valve firmly against its seat and draws purging air from the air preparation unit into and through the ozone generator and first check valve until the pressure in the reservoir reaches $-1.5$ psi, the cracking pressure of the first check valve. At this time the first check valve closes, trapping the purged ozone in the reservoir. Since the vacuum reservoir has thus gone through a pressure change of approximately 0.5 atmosphere ($9-1.5=7.5$ psi $=0.5$ atm), then the volume of air which has purged the ozone generator is equal to approximately one-half of the total volume of the reservoir.

While this invention has been described in connection with preferred embodiments thereof, it is obvious that modifications and changes therein may be made by those skilled in the art to which it pertains without departing from the spirit and scope of this invention. Accordingly, the scope of this invention is to be limited only by the appended claims.

What is claimed is:

1. An apparatus for regulating flow in an ozone generation system, and for automatically purging residual ozone upon shutdown of said ozone generation system, said apparatus comprising:

an ozone generator;

a negative pressure ozone injector device connected by a fluid flow line to said ozone generator;

a first check valve member interposed in said fluid flow line between said ozone generator and said negative pressure ozone injector device;

a vacuum reservoir interposed in said fluid flow line between said first check valve member and said negative pressure ozone injector device;

a second check valve member interposed in said fluid flow line between said vacuum reservoir and said negative pressure ozone injector device; and a restrictive orifice member interposed in said fluid flow line between said ozone generator and said vacuum reservoir;

wherein while said negative pressure ozone injector device is in operation, a pressure differential exists across said restrictive orifice, with a lower pressure in said vacuum reservoir and a higher pressure in said ozone generator; and upon shutdown of said ozone generator and said negative pressure ozone injector device, said lower pressure causes said second check valve to close, and said pressure differential causes said residual ozone to be drawn from said ozone generator into said vacuum reservoir until said pressure differential becomes nearly equalized, whereupon said first check valve automatically closes.

2. The apparatus of claim 1 wherein said first check valve member comprises said restrictive orifice member.

3. The apparatus of claim 1 wherein said restrictive orifice member comprises a valve.

4. The apparatus of claim 1 wherein said restrictive orifice member is interposed in said fluid flow line between said first check valve member and said vacuum reservoir.

5. The apparatus of claim 1 wherein said restrictive orifice member is interposed in said fluid flow line between said ozone generator and said first check valve member.

6. The apparatus of claim 1 wherein said vacuum reservoir comprises a vacuum bottle and the length of said fluid flow line between said restrictive orifice member and said second check valve member.

7. The apparatus of claim 6 wherein said vacuum bottle has a single opening.

8. The apparatus of claim 6 wherein said vacuum bottle has a separate entrance and exit.

9. The apparatus of claim 1 wherein said first check valve member, restrictive orifice member, vacuum reservoir, and second check valve member are each constructed of an ozone inert material.

10. The apparatus of claim 1 wherein said negative pressure ozone injector device comprises a venturi.

11. A method for regulating flow in an ozone generation system, and for automatically purging residual ozone upon shutdown of said ozone generation system, said method comprising:
providing an ozone generator;
providing a negative pressure ozone injector device connected by a fluid flow line to said ozone generator;
providing a first check valve member in said fluid flow line between said ozone generator and said negative pressure ozone injector device;
providing a vacuum reservoir in said fluid flow line between said first check valve member and said negative pressure ozone injector device;
providing a second check valve member in said fluid flow line between said vacuum reservoir and said negative pressure ozone injector device; and
providing a restrictive orifice member in said fluid flow line between said ozone generator and said vacuum reservoir;
such that while said negative pressure ozone injector device is operating, a pressure differential is created across said restrictive orifice, with a lower pressure in said vacuum reservoir, and a higher pressure in said ozone generator; and upon shutdown of said ozone generator and said negative pressure ozone injector device, said second check valve closes, and said pressure differential causes said residual ozone to be drawn from said ozone generator into said vacuum reservoir until said pressure differential becomes generally equalized, whereupon said first check valve automatically closes, thereby preventing back-flow of said residual ozone into said ozone generator.

12. The method of claim 11 wherein said first check valve member comprises said restrictive orifice member.

13. The method of claim 11 wherein said restrictive orifice member comprises a valve.

14. The method of claim 13 including adjusting said valve to adjust the flow of ozone.

15. The method of claim 11 including providing said restrictive orifice member in said fluid flow line between said first check valve member and said vacuum reservoir.

16. The method of claim 11 including providing said restrictive orifice member in said fluid flow line between said ozone generator and said first check valve member.

17. The method of claim 11 wherein said vacuum reservoir comprises a vacuum bottle and the length of said fluid flow line between said restrictive orifice member and said second check valve member.

18. The method of claim 11 wherein said first check valve member, restrictive orifice member, vacuum reservoir, and second check valve member are each constructed of an ozone inert material.

19. The method of claim 11 wherein said negative pressure ozone injector device comprises a venturi.

* * * * *